US012271240B1

(12) United States Patent
Johnson et al.

(10) Patent No.: US 12,271,240 B1
(45) Date of Patent: Apr. 8, 2025

(54) SCOPE CABINET

(71) Applicant: CLINICAL CHOICE, LLC, Greensboro, NC (US)

(72) Inventors: Joseph Johnson, Greensboro, NC (US); Scott Johnson, High Point, NC (US); Bret Reynolds, Greensboro, NC (US)

(73) Assignee: Clinical Choice, LLC, Greensboro, NC (US)

( * ) Notice: Subject to any disclaimer, the term of this patent is extended or adjusted under 35 U.S.C. 154(b) by 413 days.

(21) Appl. No.: 18/052,682

(22) Filed: Nov. 4, 2022

(51) Int. Cl.

| | |
|---|---|
| ***G06F 1/20*** | (2006.01) |
| ***A61B 50/20*** | (2016.01) |
| ***B01D 46/58*** | (2022.01) |
| ***F24F 1/0071*** | (2019.01) |
| *A61B 50/10* | (2016.01) |

(52) U.S. Cl.
CPC ................ *G06F 1/20* (2013.01); *A61B 50/20* (2016.02); *B01D 46/58* (2022.01); *F24F 1/0071* (2019.02); *A61B 2050/105* (2016.02); *B01D 2273/30* (2013.01)

(58) Field of Classification Search
CPC ........... H05K 7/16; H05K 5/00; H04M 1/022; G06F 1/20; A61B 50/20; A61B 2050/105; F24F 1/0071; B01D 46/58; B01D 2273/30; A47B 46/005; A47B 5/00; A47B 5/006; A47B 5/04; A47B 57/34; A47B 57/54; A47B 57/545; A47B 77/10; A47B 88/433; A47B 96/06; A47B 96/07; A47B 96/14; A47B 96/1441
See application file for complete search history.

(56) References Cited

U.S. PATENT DOCUMENTS 3,857,623 A * 12/1974 Schneller ............. A47B 46/005 312/294
4,662,689 A * 5/1987 Chatterson ............ E05B 65/462 70/120
6,969,129 B2 * 11/2005 Ludwig ................. E05B 65/464 312/328
8,919,894 B1 * 12/2014 Pachmayr ............ A47B 46/005 312/7.2
9,693,478 B2 * 6/2017 Ivey ..................... A47B 46/005
10,561,235 B1 * 2/2020 Abbott ................... A47B 77/10
2002/0101143 A1 * 8/2002 Crooks .................. A47B 88/43 312/334.7
2007/0069614 A1 * 3/2007 Waugh ................. A47B 46/005 312/245

(Continued)

*Primary Examiner* — Amir A Jalali
(74) *Attorney, Agent, or Firm* — Tuggle Duggins P.A.; Blake P. Hurt; Reinier R. Smit

(57) ABSTRACT

A scope cabinet that defines a cavity configured to receive a medical device, such as a gastroscope or endoscope, therein. The scope cabinet includes a detachable, cradle panel disposed on a panel within the cavity. The cradle panel forms a plurality of elongated slats. The scope cabinet further includes an adjustable arm that is configured to be releasably fastened at a point along one of the elongated slats. The adjustable arm includes a plurality of fingers and is configured to support a medical device. The scope cabinet also includes a removable shelf disposed within the cavity having an air-circulating unit disposed on top of the shelf. The scope cabinet has a rear panel that defines removable subsections. The cradle panel is attached to one of the subsections nearest a top panel of the scope cabinet but below the removable shelf.

15 Claims, 8 Drawing Sheets

(56) References Cited

U.S. PATENT DOCUMENTS

| | | | | |
|---|---|---|---|---|
| 2007/0126321 | A1* | 6/2007 | Waugh | A47B 46/00 312/245 |
| 2011/0235249 | A1* | 9/2011 | Bustle | G06F 1/182 361/679.01 |
| 2019/0387874 | A1* | 12/2019 | Held | A47B 46/005 |

* cited by examiner

SCOPE CABINET

FIELD OF THE INVENTION

The disclosure herein pertains to storage cabinets generally, and particularly pertains to storage cabinets for medical devices such as gastroscopes, colonoscopes, and other specialty endoscopes that assist in the maintenance of the scopes and provides for pre- and post-sterilization storage for the scopes.

DESCRIPTION OF THE PRIOR ART AND OBJECTIVES OF THE INVENTION

Medical devices are sensitive equipment that require sterilization, maintenance, and storage in between procedures. Improper storage of a medical device may lead to damage from accidents or the environment, theft, misplacement, microorganism colonization, dust buildup, and more, all of which may require replacement or servicing of the device resulting in unnecessary expenses. Proper storage equipment for medical devices is essential for any medical practice. Some medical devices may be used frequently whereas other medical devices may be used relatively infrequently; therefore, it may be desirable for storage devices to provide post-sterilization storage capabilities, otherwise known as storage period between the last cleaning/sterilization and the next procedure.

In addition to post-sterilization storage capabilities, pre-sterilization storage may be desirable to store used medical devices until after the procedure is completed, so that they are easily accessible for cleaning and sterilization. During periods of post-sterilization or pre-sterilization storage, storage structures may be desirable to hold portions of a medical device so as to prevent entanglement of cables and cords, and help organize the interior of the storage device, and prevent cross-contamination. Storage structures may hold or support a medical device for a period of time in between uses or in between a use and the end of a procedure. The storage structures of the prior art are insufficient at least because their positioning within the storage device is often unalterable, the storage structures of the prior art are often overly generalized to serve a purpose and thereby may not serve certain medical devices effectively, and the storage structures of the prior art are often not exchangeable or replaceable with different storage structures that could better serve a particular medical device.

Medical devices need to be sterilized and cleaned after a procedure. Sterilization and cleaning may be accomplished in a variety of ways including (but not limited to) using moist heat (steam), dry heat, radiation, ethylene oxide gas, vaporized hydrogen peroxide, chlorine dioxide gas, vaporized peracetic acid, nitrogen dioxide, and other methods and combinations thereof. Of particular concern are methods involving harsh chemicals. Harsh cleaning chemicals that vaporize and are released into the air in sufficiently high concentrations may present both health concerns to medical personnel and patients breathing in the air without breathing protection. Likewise, harsh cleaning chemicals if left on the surfaces of medical devices or at sufficient concentrations in the ambient air may lead to degradation and damage of medical devices. The storage devices of the prior art fail to provide mechanisms that can assist in the vaporization of cleaning chemicals off the surface of medical devices and that can dissipate chemical vapors from within the storage device, preventing the buildup of cleaning chemical vapors in high concentrations.

Many storage solutions for medical devices such as gastroscopes and endoscopes exist in the prior art. Many of these solutions provide storage capabilities to store one or more of these scopes. However, these solutions provide limited capabilities beyond storage between patient procedures. There is a need for a scope cabinet that has the capacity for post-sterilization and pre-sterilization storage of one or more different internal scopes between patient procedures, is customizable and modular to fit a certain user's needs, assists with maintenance and organization of medical devices such as these internal scopes, and decreases health and safety threats.

Thus, in view of the problems and disadvantages associated with prior art devices, the present disclosure was conceived and one of its objectives is to provide a scope cabinet with a detachable cradle panel defining an elongated slat configured to receive an adjustable arm for holding medical instruments, wherein the cradle panel is disposed within the cavity of the scope cabinet.

It is another objective of the present disclosure to provide a scope cabinet with an adjustable arm with a finger for holding and/or supporting an internal scope, wherein the arm is disposed within a cavity formed by the cabinet.

It is still another objective of the present disclosure to provide a scope cabinet with an adjustable arm with a plurality of fingers for holding and/or supporting an internal scope, wherein the arm is disposed within a cavity of the cabinet.

It is also an objective of the present disclosure to provide a scope cabinet with an adjustable arm with a plurality of fingers, wherein the plurality of fingers and adjustable arm are configured to receive an endoscope, gastroscope, or similar medical instrument.

It is yet another objective of the present disclosure to provide a scope cabinet with a cradle panel defining a plurality of elongated slats and a plurality of openings, the slats and openings are arranged in an alternating pattern.

It is a further objective of the present disclosure to provide a scope cabinet with a cradle panel defining an elongated slat configured to receive a fastener of an adjustable arm, the cradle panel also defining an opening, wherein the fastener is threaded through a base of the adjustable arm and through the elongated slat and tightened, fixing the base of the adjustable arm in place and preventing movement of the base along a longitudinal axis of the elongated slat.

It is yet another objective of the present disclosure to provide a scope cabinet with a rear panel that defines removable subsections that are arranged in series along a longitudinal axis defined by the scope cabinet, wherein the cradle panel is disposed within the cavity and attached to an interior surface of one of the removable subsections.

It is still a further objective of the present disclosure to provide a scope cabinet that defines a cavity with a removable platform disposed within the cavity.

It is yet a further objective of the present disclosure to provide a scope cabinet with an electric fan that is positioned above a plurality of holes defined through the removable platform so that gases from a portion of the cavity above the removable platform may be transferred to a portion of the cavity below the removable platform, creating positive pressure within the portion of the cavity below the removable platform.

It is another objective of the present disclosure to provide an air circulating unit to provide positive pressure within the portion of the cavity below the removeable platform so that gases are pushed through an opening positioned at the bottom of the cabinet and an opening positioned at the front of the cabinet below the door.

It is yet still a further objective of the present disclosure to provide a scope cabinet for short or long term storage of medical instruments that includes an air circulating assembly to assist with displacement of vaporized cleaning chemicals from within the cabinet.

Various other objectives and advantages of the present disclosure will become apparent to those skilled in the art as a more detailed description is set forth below.

SUMMARY OF THE INVENTION

The aforesaid and other objectives are realized by providing a scope cabinet including a door, two side panels, a rear panel, a top panel, and a bottom panel, assembled to form a container with a cavity therein. The cavity is configured to receive a medical device such as an internal scope therein. The door and rear panel are positioned opposite one another, and the pair of side panels are positioned opposite one another. The scope cabinet includes four trusses positioned at the connections between the pair of side panels, the rear panel, and the door, and extend along a longitudinal axis defined by the scope cabinet to each be at least as long as one of the side panels or the rear panel. The scope cabinet includes an air-circulating unit and a power unit. The air-circulating unit includes four electric fans, two filter holders, and two filters. The electric fans are positioned in groups of two, with all four fans in series. The filter holders are each sized and shaped to cover two electric fans and are each positioned over two of the four electric fans. The filter holders are also sized and shaped to each receive one of the two filters. The filter holders each define an opening sized and positioned so that air pulled by the electric fans flows through the filters then through the openings, then through the electric fans filtering the air from the ambient environment to prevent particulates from being disposed on an internal scope contained within the cavity. The power unit includes a power distribution box power source, and power cables, the power source is electrically connected to the power distribution box via a power cable which is in turn connected to the electric fans via the power cables. The power unit may also include two elongated LED bars for illuminating the cavity.

The scope cabinet includes a shelf with a removable platform. The power unit and air-circulating unit are positioned on the removable platform. The shelf and the platform are positioned near the top panel of the cavity but at least distanced enough from the top panel to accommodate the air-circulating unit and the power unit. The removable platform includes four openings, wherein one of the four electric fans are positioned over each opening so that gases from a portion of the cavity above the removable shelf are pulled by the electric fans through the filters, thereby filtering the air, preferably removing pathogens, allergens and other particulates from the air, and pushed by the electric fans through the openings of the removable shelf into the portion of the cavity below the removable shelf.

The rear panel of the scope cabinet is divided into removable subsections that are arranged in series along a longitudinal axis of the scope cabinet. The scope cabinet further comprises an adjustable arm and a detachable cradle panel that is disposed within the cavity and is positioned on a removable subsection of the rear panel that is positioned nearest the top panel but below the shelf. The detachable cradle panel includes a plurality of elongated slats that are configured to receive a fastener. The adjustable arm includes a beam with a base at one end, a first plurality of fingers at the other end, and a second plurality of fingers between the base and the first plurality of fingers. The adjustable arm is configured to receive an internal scope. In the preferred embodiment, the medical device may be a gastroscope, colonoscope, endoscope, or similar internal scope. The adjustable arm includes two fasteners that are inserted through the base and through the elongated slat that secures the adjustable arm to the cradle panel at a desired point along the elongated slat.

DETAILED DESCRIPTION OF THE PREFERRED EMBODIMENT AND OPERATION OF THE INVENTION

Figure 1:
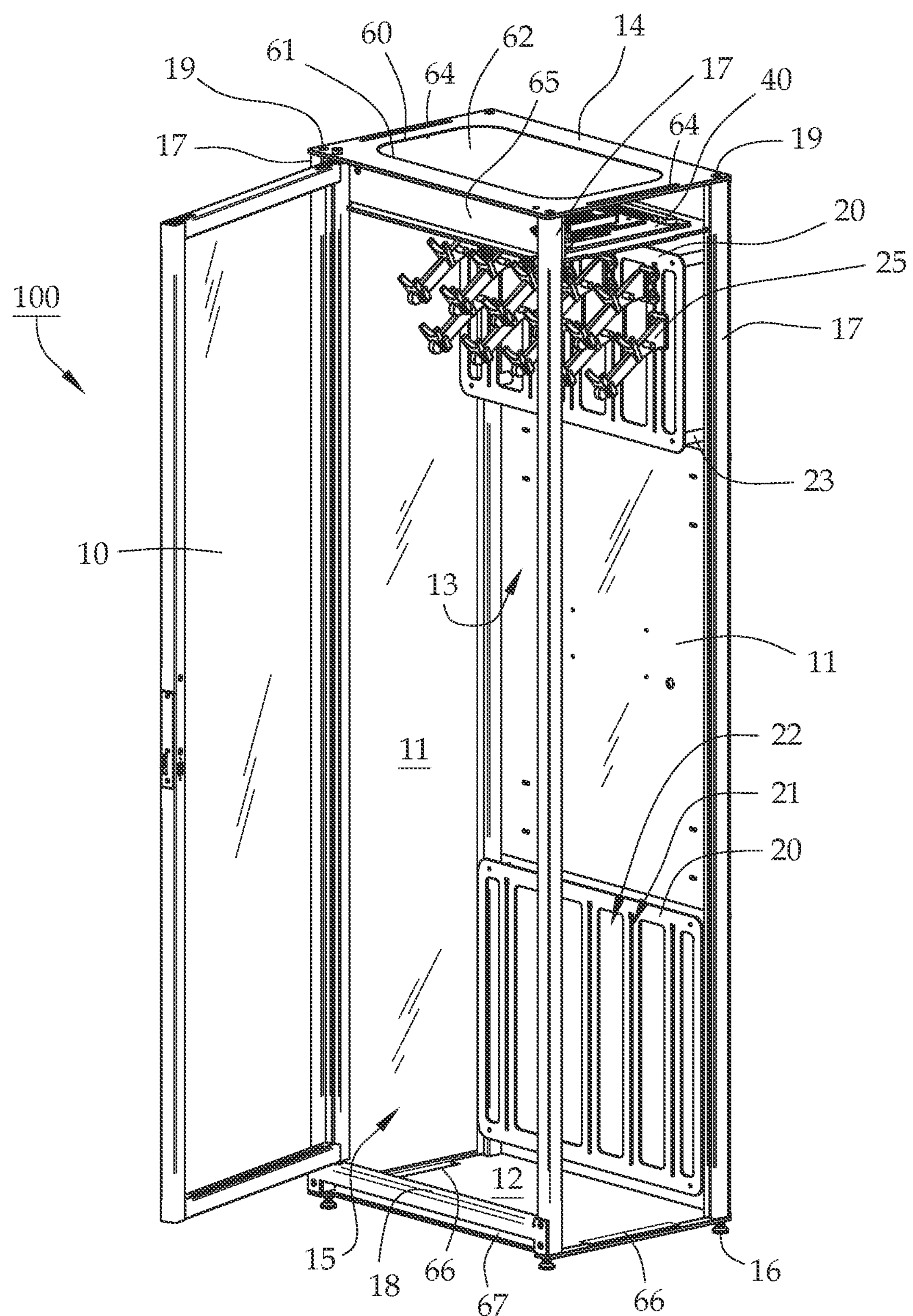
FIG. 1 shows a perspective view of the scope cabinet showing a door, two side panels, and a rear panel, disposed within a cavity are two cradle panels, showing the door in an open position.

Various exemplary embodiments of the present disclosure are described below. Use of the term "exemplary" means illustrative or by way of example only, and any reference herein to "the disclosure" is not intended to restrict or limit the disclosure to exact features or step of any one or more of the exemplary embodiments disclosed in the present specification. References to "exemplary embodiment", "one embodiment", "an embodiment", "various embodiments", and the like may indicate that the embodiment(s) of the disclosure so described may include a particular feature, structure, or characteristic, but not every embodiment necessarily incudes the particular feature, structure, or characteristic. Further, repeated use of the phrase "in one embodiment", "in an exemplary embodiment", or "in an alternative embodiment" do not necessarily refer to the same embodiment, although they may.

It is also noted that terms like "preferably", "commonly", and "typically" are not utilized herein to limit the scope of the disclosure or to imply that certain features are critical, essential, or even important to the structure or function of the disclosure. Rather, these terms are merely intended to highlight alternative or additional features that may or may not be utilized in a particular embodiment of the present disclosure.

The present disclosure is described more fully hereinafter with reference to the accompanying figures, in which one or more exemplary embodiments of the disclosure are shown. Like numbers used herein refer to like elements throughout. The disclosure may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limited as to the scope of the disclosure, and any and all equivalents thereof. Moreover, many embodiments such as adaptations, variations, modifications, and equivalent arrangements will be implicitly disclosed by the embodiments described herein and fall within the scope of the instant disclosure.

Although specific terms are employed herein, they are used in a generic and descriptive sense only and not for the purposes of limitation. Unless otherwise expressly defined herein, such terms are intended to be given their broad, ordinary, and customary meaning not inconsistent with that applicable in the relevant industry and without restriction to any specific embodiment hereinafter described. As used herein, the article "a" is intended to include one or more items. Where only one item is intended, the terms "one and only one", "single", or similar language is used. When used herein to join a list of items, the term "or" denotes at least one of the items but does not exclude a plurality of items of the list.

For exemplary methods or processes of the disclosure, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present disclosure.

Additionally, any references to advantages, benefits, unexpected results, or operability of the present disclosure are not intended as an affirmation that the disclosure has previously been reduced to practice or that any testing has been performed. Likewise, unless stated otherwise, use of verbs in the past tense (present perfect or preterit) is not intended to indicate or imply that the disclosure has previously been reduced to practice or that any testing has been performed.

As used herein, the term "internal scope" is defined as any medical device for entering a body cavity or orifice with the intent of imaging the cavity or orifice, providing an image to medical personnel, and/or retrieving a tissue sample for biopsy.

Figure 2:
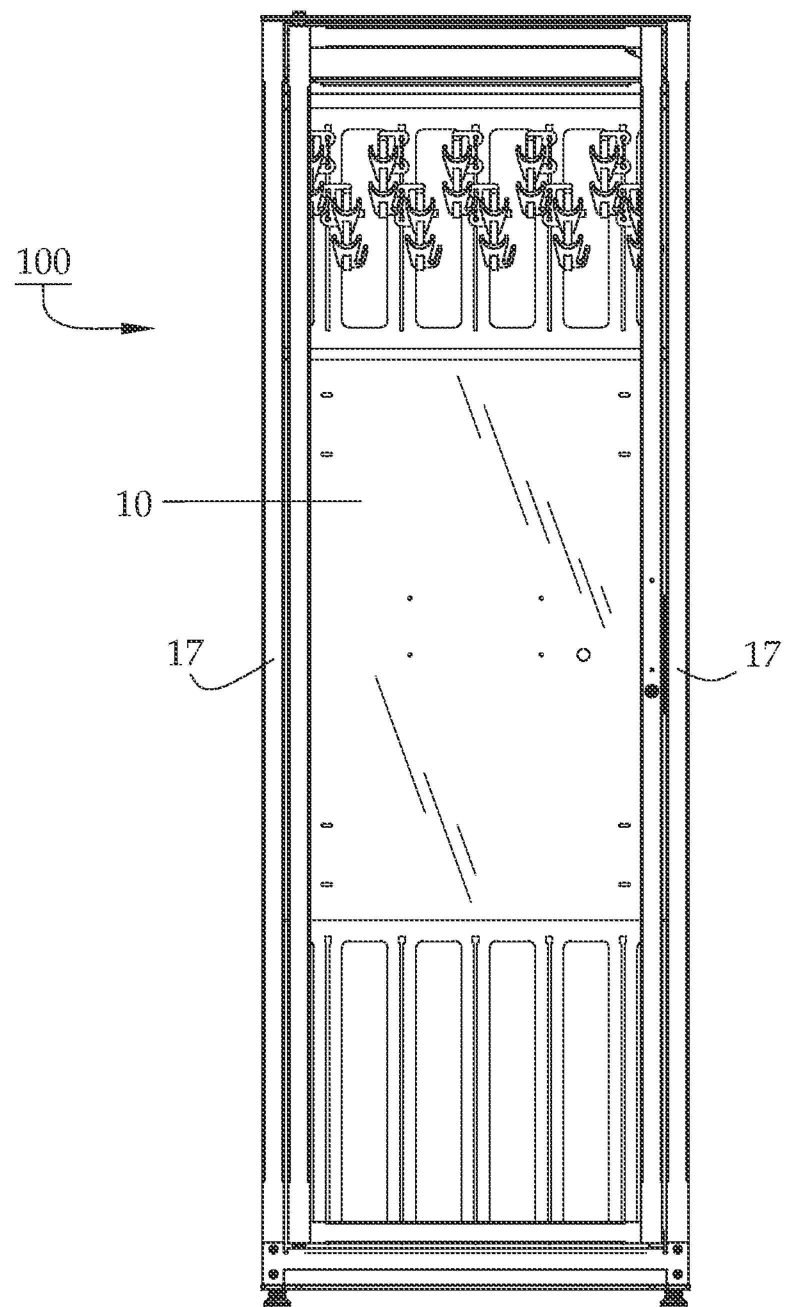
FIG. 2 depicts a plan view of the scope cabinet with the door closed.
Figure 3:
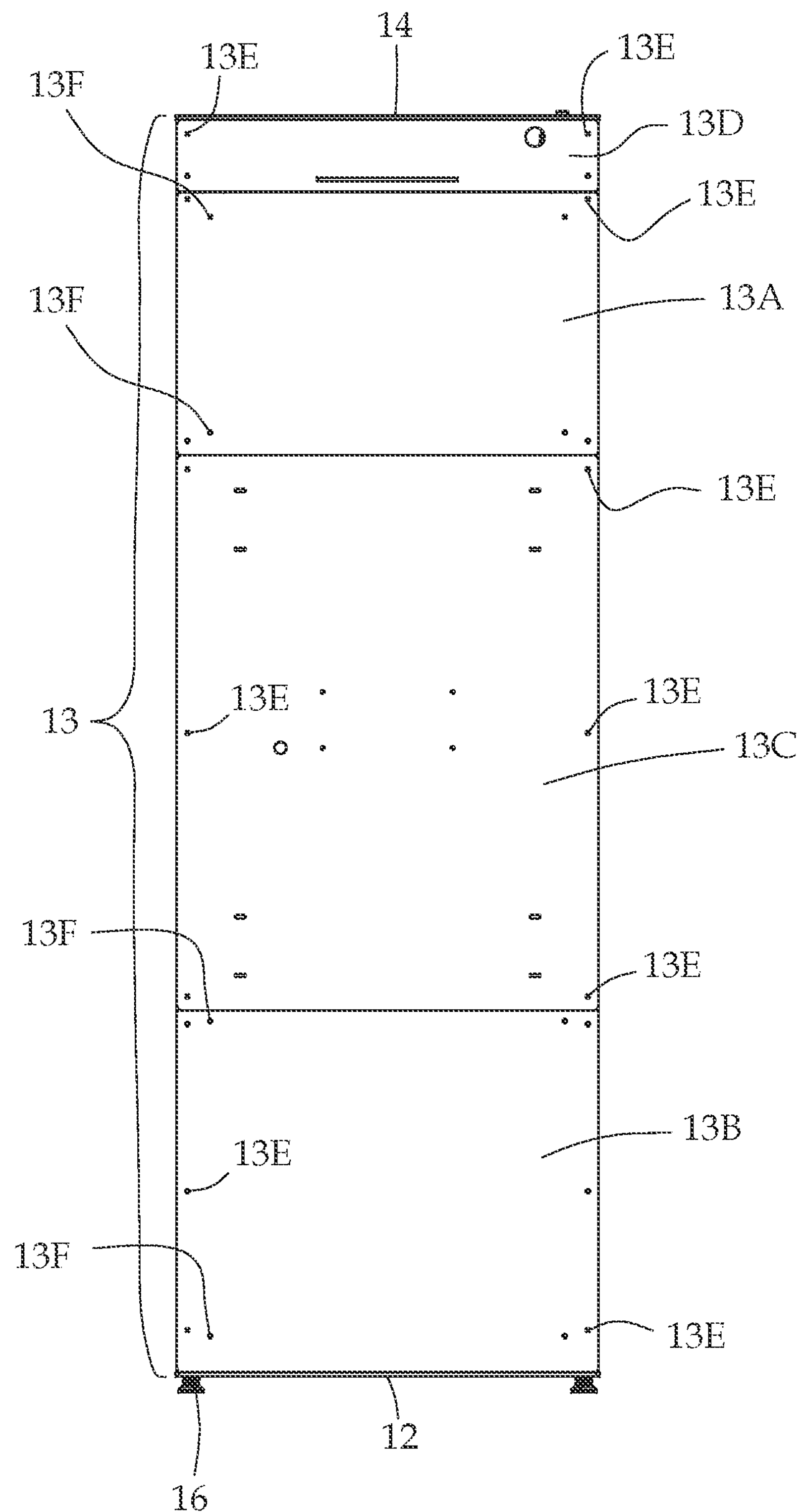
FIG. 3 pictures a plan view of the rear panel of the scope cabinet.

For a better understanding of the disclosure and its operation, turning now to the drawings, referring to FIGS. 1, 2, and 3, the scope cabinet 100 includes a door 10 and defines a side panel 11, a bottom panel 12, a rear panel 13, and a top panel 14. The scope cabinet 100 is preferably sized and shaped to receive one or more medical devices such as an internal scope therein. The door 10, side panel 11, bottom panel 12, rear panel 13, and top panel 14 are assembled to form a container which defines cavity 15. The cavity 15 is preferably sized and shaped to receive an internal scope therein. In some embodiments, it may be desirable for the door 10, side panel 11, bottom panel 12, and rear panel 13, to all be substantially the same size and shape, i.e., similar rectangles.

In a preferred embodiment, the rear panel 13 and the door 10 are positioned opposite one another. The scope cabinet 100 preferably defines two side panels 11, wherein the rear panel 13 and door 10 are each connected to one side of each of the two side panels 11, forming a rectangular tube. In some embodiments, the scope cabinet 100 includes four trusses 17 each sized and shaped to extend at least the longitudinal length of the side panel 11 and/or rear panel 13. The trusses 17 are positioned at the connections between the door 10, side panels 11, and rear panel 13 to increase the structural integrity of scope cabinet 100. In certain embodiments, the two trusses 17 nearest the door 10 form a portion of the frame of the door 10, and the scope cabinet 100 may include a horizontal truss 18 that is positioned near bottom panel 12 and forms a horizontal portion of the frame of the door 10 nearest bottom panel 12. In alternative embodiments, the connections between the door 10, side panels 11, and rear panel 13 may not include trusses 17, instead relying on other structures to maintain the form of the scope cabinet 100 such as (but not to be construed as a limitation) fasteners or welding. In the preferred embodiment, the top panel 14 is configured to be connected at a top portion of the rectangular tube of scope cabinet 100 to the sides of the side panels 11, door 10, and rear panel 13; and bottom panel 12 is configured to be connected at a bottom portion of the rectangular tube to the sides of the side panels 11, door 10, and rear panel 13. With the bottom panel 12 and top panel 14 attached, a rectangular prism is preferably formed. In one or more embodiments, the bottom panel 12 and top panel 14 may be fastened and/or affixed to each of the four trusses 17 and may include corresponding fastener openings 19.

In one or more embodiments, at least a portion of one or more of the door 10, side panel 11, bottom panel 12, and rear panel 13 is formed from a transparent material so that medical personnel may view contents within the cavity 15. One or more of the door 10 and panels 11, 12, 13 may be formed from materials such as (but not limited to): acrylic, glass, or a non-porous, transparent material. Ideally, at least a portion of the door 10 and a portion of two side panels 11 are formed from a transparent material. In one or more embodiments, the bottom panel 12, rear panel 13, and/or top panel 14 may be formed from a metal, metal alloy, or hard, opaque material. In one or more embodiments, the scope cabinet 100 may include a structure or mechanism for transportation 16 that depends from bottom panel 12. The structure or mechanism for transportation 16 may be selected from a group consisting of wheels, glides, slides, and tires, and combinations thereof. It is desirable that the scope cabinet 100 is easily moveable so as to limit the minimum number of medical personnel required to safely and efficiently move the scope cabinet 100 from one location to another, often moving the scope cabinet 100 from a point of care to a medical device cleaning area.

As best seen in FIG. 3, the scope cabinet 100 includes a rear panel 13. In one or more embodiments, the rear panel 13 may be divided and define removable subsections. In some embodiments, there are two subsections, subsection 13*a* positioned nearest top panel 14 but below a removable platform 40 that is disposed within cavity 15 and subsection 13*b* positioned nearest bottom panel 12. In certain embodiments, there may be a third subsection, subsection 13*c* that is positioned between 13*a* and 13*b*. In the preferred embodiment, there is a fourth section, subsection 13*d*, that is positioned nearest top panel 14 but above the removable platform 40. Additional subsections 13 (not shown) are considered within the scope of the instant disclosure. Subsection 13*d* may be removed to reveal and facilitate access to content disposed on top of removable platform 40, and in some embodiments the removable platform 40 may be removed through the opening formed from the removable subsection 13*d*. In any of the embodiments mentioned herein, the rear panel 13 and/or its subsections 13*a*, 13*b*, 13*c*, and 13*d*, may preferably include fastener holes 13*e* configured to receive a fastener so as to attach the panel 13 and/or its subsections 13*a*, 13*b*, 13*c*, and 13*d* to the connections between the rear panel 13 and either side panel 11, and ideally attach the panel 13 and/or its subsections 13*a*, 13*b*, 13*c*, and 13*d* to the two trusses 17 positioned at the connections between the rear panel 13 and the two side panels 11. One or more of fasteners 13*e* facilitate the easy removal and replacement of the rear panel 13 and/or its subsections 13*a*, 13*b*, 13*c*, and 13*d*. Removal of certain subsections 13*a*, 13*b*, 13*c*, and/or 13*d*, may be desirable to access certain components of the scope cabinet 100. It should be understood that subsections 13*a*, 13*b*, and 13*c* and additional subsections (not shown) may be configured to receive a cradle panel 20 (as seen in FIG. 1), and under some circumstances it may be desirable to remove one of the subsections 13*a*, 13*b*, 13*c* and additional subsections (not shown) with a cradle panel 20 still attached to the removed subsection. Each of the subsections 13*a*, 13*b*, 13*c* and additional subsections (not shown) may also be configured to receive other systems and machines (not shown) related to internal scopes, such as systems to dry the interiors or exteriors of internal scopes.

Figure 4:
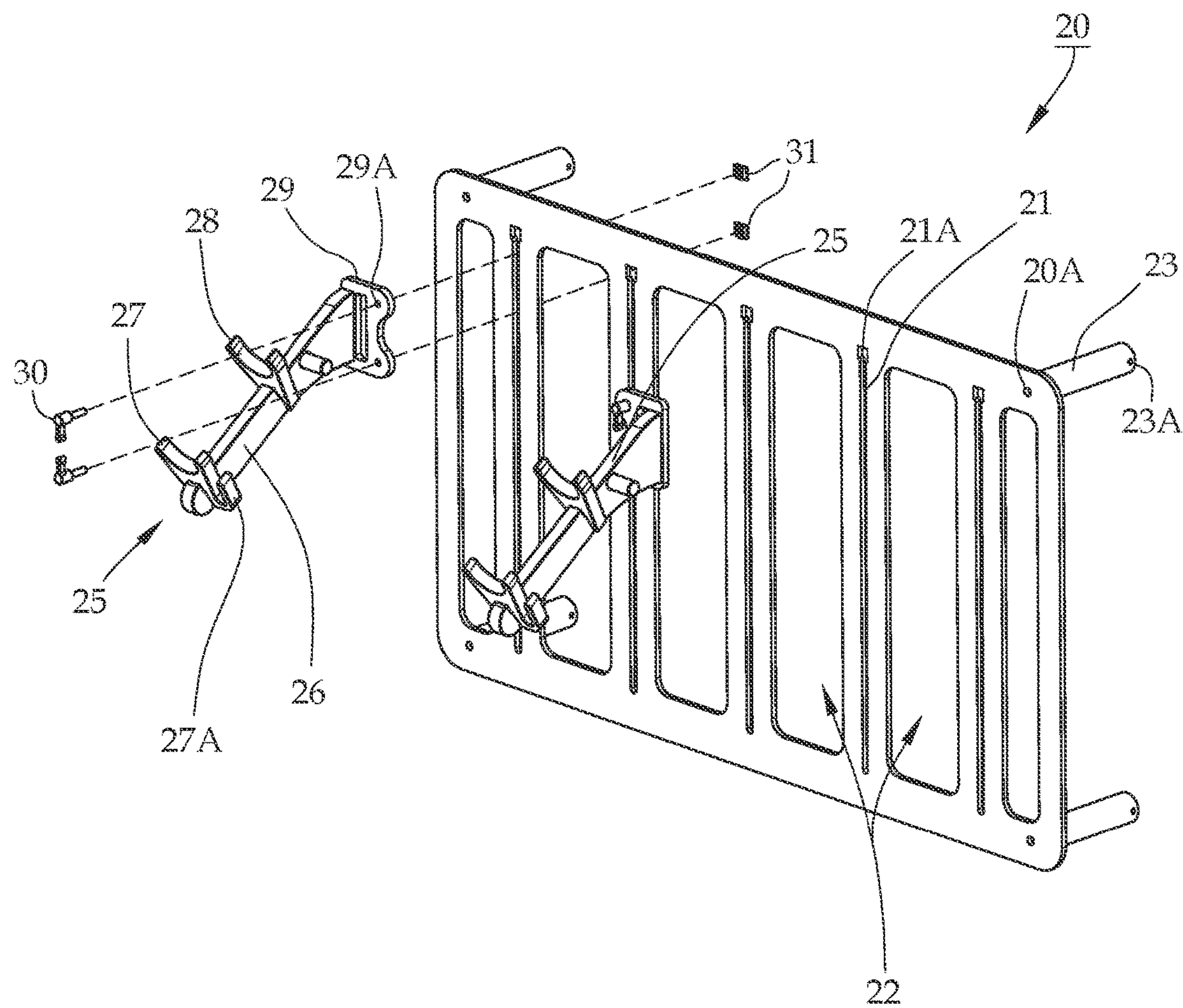
FIG. 4 depicts a perspective view of a cradle panel with two adjustable arms that would be attached to a subsection of the rear panel.

Referring to FIGS. 1, 2, and 4, the scope cabinet 100 further comprises a detachable cradle panel 20 that may be removed, reattached, and exchanged with another detachable cradle panel 20. The cradle panel 20 preferably defines an elongated slat 21. The scope cabinet 100 may further comprise an adjustable arm 25 that is configured to be fastened at a point along the elongated slat 21. The cradle panel 20 is disposed within cavity 15 and is fastened and/or affixed to rear panel 13. The cradle panel 20 is configured to support an internal scope during periods of pre- or post-sterilization storage. It should be understood that post-sterilization storage may include periods when the internal scope is drying after having been sterilized or otherwise cleaned.

In one or more embodiments, the elongated slat 21 is configured to extend along a longitudinal axis defined by rear panel 13. In other embodiments, the elongated slat 21 is configured to extend along a lateral axis defined by the rear panel 13. In one or more embodiments, the elongated slat 21 includes a fastener opening 21*a* sized and shaped to receive a fastener and positioned at an end of the elongated slat 21, preferably the end of the elongated slat 21 nearest the top panel 14 to prevent fasteners from inadvertently exiting the elongated slat 21 through the fastener opening 21*a*. In the preferred embodiment, the cradle panel 20 defines a plurality of elongated slats 21. The cradle panel 20 also may define an opening 22 configured to provide medical personnel access to a side of the cradle panel 20 that is facing the rear panel 13, such access may be necessary in some circumstances to adjust medical devices like internal scopes or reposition the adjustable arm 25. In the preferred embodiment, the opening 22 is approximately the same length as the elongated slat 21. In one or more embodiments, the cradle panel 20 defines a plurality of openings 22 that are arranged in an alternating pattern with a plurality of elongated slats 21. The preferred cradle panel 20 is rectangular in shape and includes four tubular members 23 each configured to be affixed and/or fastened to one of the corners of the cradle panel 20 by inserting a fastener (not shown) through fastener hole 20*a* then through a corresponding fastener hole (not shown) of the tubular member 23. In some embodiments, the tubular members 23 are further configured to be affixed to the rear panel 13 and/or one of subsections 13*a*, 13*b*, 13*c*. In other embodiments, the tubular members 23 and the rear panel 13 and/or one of subsections 13*a*, 13*b*, 13*c*, define corresponding fastener holes, 23*a* and 13*f* respectively, configured to receive a fastener therein to facilitate the attachment of the cradle panel 20 to the rear panel 13 and/or one of subsections 13*a*, 13*b*, 13*c*. In the preferred embodiment, the cradle panel 20 is affixed and/or attached to subsection 13*a*. In other embodiments, a first cradle panel 20 is affixed and/or attached to subsection 13*a* and a second cradle panel 20 is affixed and/or attached to subsection 13*b*. The cradle panel 20 may be removed from the cavity of the scope cabinet 100 by either unfastening the tubular members 23 of cradle panel 20 from rear panel 13 and removing the cradle panel 20 through the door 10 or by unfastening the rear panel 13 and/or one of subsections 13*a*, 13*b*, 13*c* from the two trusses 17 nearest rear panel 13 and removing the rear panel 13 and/or one of subsections 13*a*, 13*b*, 13*c* with the cradle panel 20 still attached thereto. Although not shown, the rear panel 13 and/or any of the subsections 13*a*, 13*b*, 13*c* and additional subsections (not shown), may be configured to receive systems and machines (not shown) related to internal scopes within the cavity 15, such as but not limited to systems that facilitate the drying of the lumen of an internal scope.

As seen in FIG. 4, the scope cabinet 100 includes an adjustable arm 25 that is configured to be releasably fastened to the cradle panel 20 at a point along the elongated slat 21. In the preferred embodiment, the adjustable arm 25 is comprised of a beam 26 and a base 29. The beam 26 is configured so that one end of the beam 26 is attached to the base 29. In some embodiments, the adjustable arm 25 may be configured to be adjustable about the base 29. The adjustable arm 25 preferably includes a first finger 27 and may include a plurality of first fingers 27. The adjustable arm 25 is further configured so that the first plurality of fingers 27 is attached to the beam 26 at an end opposite to the base 29. The first plurality of fingers 27 is configured to provide support for an internal scope after being cleaned and/or sterilized. In the preferred embodiment, the first plurality of fingers 27 may include a finger 27*a* configured to support a cord or cable of an internal scope. In some embodiments, the adjustable arm 25 may include a second finger 28, and preferably a second plurality of fingers 28 to further support the medical device during periods of storage. The second plurality of fingers 28 may be positioned between the first plurality of fingers 27 and the base 29 along the beam 26. The first and/or second plurality of fingers 27, 28 may be configured to prevent entanglement of the cords of internal scopes. The scope cabinet 100 includes an arm fastener 30, preferably a ratcheting wingnut, that is configured to affix the adjustable arm 25 at a desired position along the longitudinal axis of the elongated slat 21 by inserting the arm fastener 30 through a hole 29*a* defined by base 29 and elongated slat 21, and then fastening the arm fastener 30 to a nut 31, preferably a T-nut. The position of the adjustable arm 25 along elongated slat 21 may need to be adjusted based on the internal scope (not shown) used or personal preference of the medical personnel. In some embodiments, to accommodate different sizes and shapes of internal scopes, the base 29 may be aligned with elongated slat 21, arm fastener 30 pushed through hole 29*a* and the user, not shown, can easily reach through larger opening 22 and firmly press nut 31 over the end of arm fastener 30 to securely seat within elongated slat 21. The arm fastener 30 may be a screw, bolt, pin, magnet, and other similar mechanical fasteners. In some embodiments, the scope cabinet 100 may include two or more arm fasteners 30 so as to prevent rotation of the base 29 of adjustable arm 25 about a transverse access of an arm fastener 30. Including two or more arm fasteners 30 may also increase the magnitude of force required to move the adjustable arm 25 about the longitudinal axis of the elongated slat 21 when the arm fasteners 30 are tightened. In the preferred embodiment, the scope cabinet 100 includes two arm fasteners 30 for each adjustable arm 25 and the base 29 of each arm 25 includes two holes 29*a*. It should be understood that a user may swap out the adjustable arm 25 for different adjustable arms that vary in size and shape, and/or may be specifically configured to receive and support a certain type of internal scope, such as a specialty internal scope. These different adjustable arms may have fingers positioned about the adjustable arm to support a certain type of internal scope in a particularly desirable manner or in a manner advised by the manufacturer of the internal scope. In the preferred embodiment, the elongated slat 21 and the fastener opening 21*a* facilitate the quick exchange of one adjustable arm 25 for another different or the same adjustable arm based on the needs of the user. Additionally, it should be understood that the arrangement of adjustable arms 25 about the cradle panel 20 including at what point the arm 25 is positioned along the longitudinal axis of the elongated slat 21 and on which particular elongated slat 21 that the arm 25 is placed in is based on user preference, but certain arrangements may be more beneficial for certain users based on which types and brands of internal scopes are being stored in the scope cabinet 100. It may be particularly desirable for the user to arrange the internal scopes in a manner that prevents scopes from touching one another and prevent(s) cord(s) of different or the same internal scope(s) from entangling so as to reduce the risk of spreading pathogens from one internal scope to another internal scope and to reduce the risk of damage to an internal scope.

Figure 5:
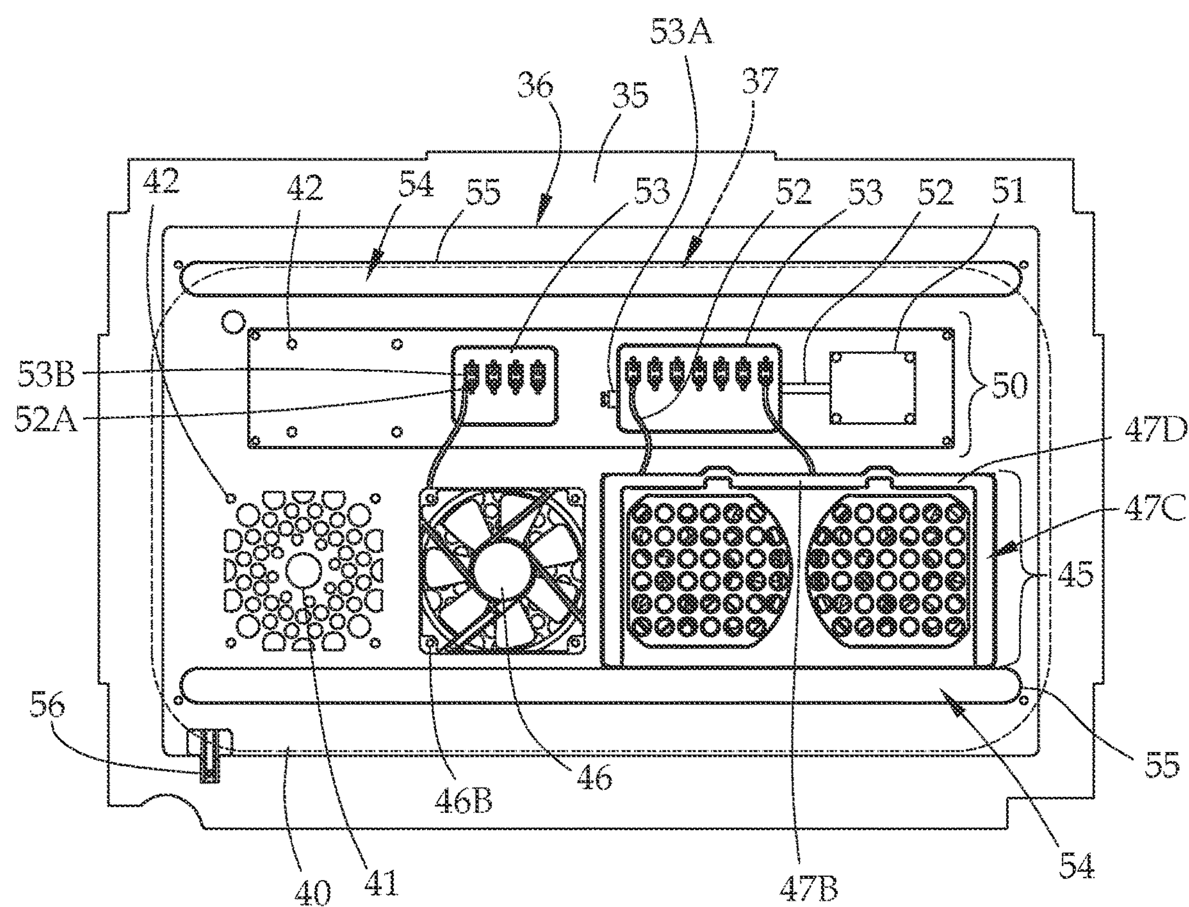
FIG. 5 demonstrates an elevated plan view of the shelf and removable platform with a power unit and air-circulation unit disposed on the removable platform.
Figure 6:
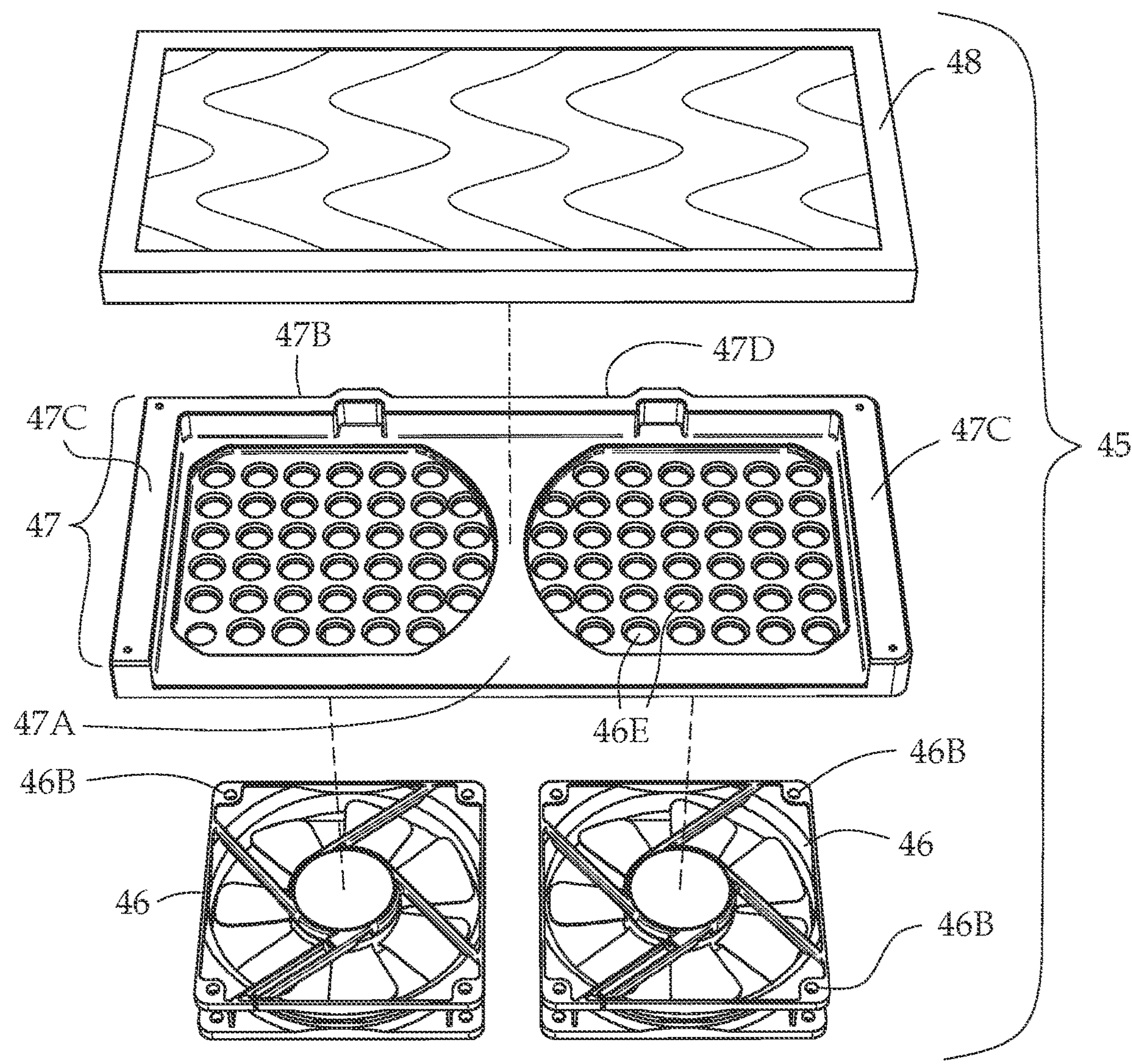
FIG. 6 shows an exploded view of a portion of the air circulating unit.
Figure 7:
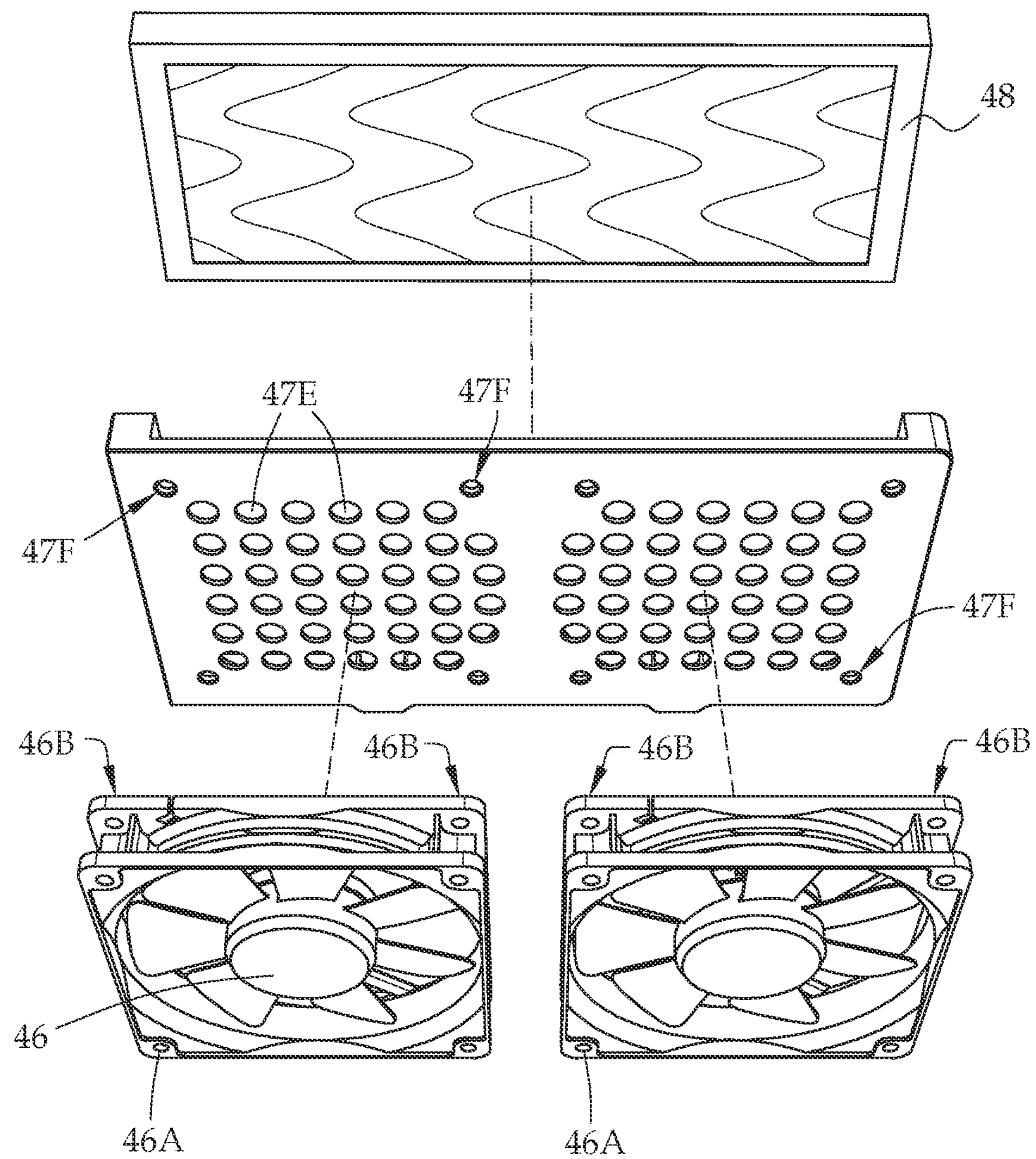
FIG. 7 illustrates the air circulating unit from FIG. 6, from a lower viewpoint.
Figure 8:
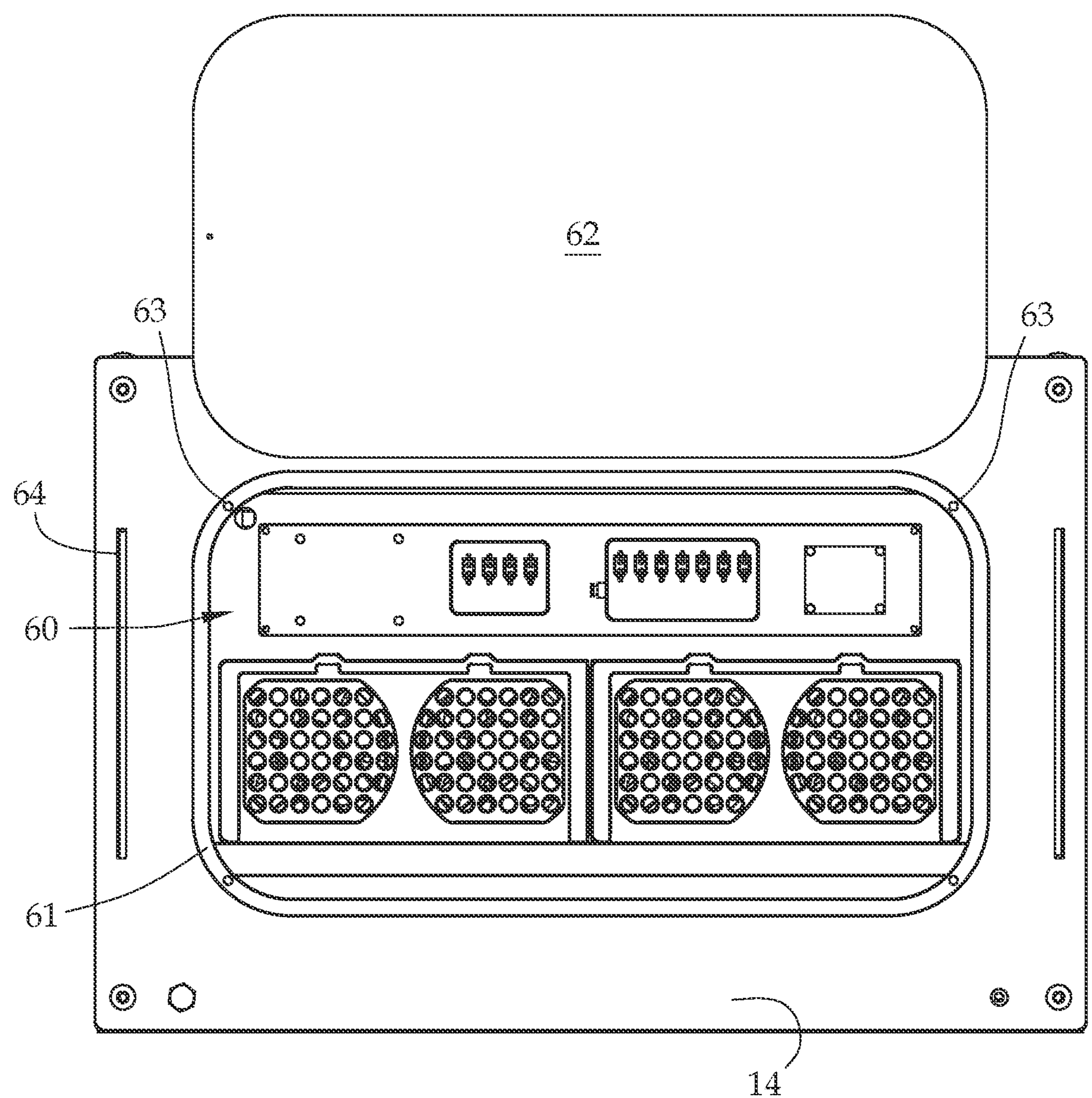
FIG. 8 features a top plan view of the scope cabinet with an access panel removed.

Now referring to FIGS. 1, 5, and 8, the preferred scope cabinet 100 further comprises a removable platform 40. The removable platform 40 is configured to be disposed within the cavity 15 at least spaced far enough from the top panel 14 so that an air circulating unit and/or a power unit may be positioned on the removable platform 40 when inside the cavity 15.

In the preferred embodiment, the scope cabinet 100 includes a shelf 35. The shelf 35 defines opening 36 sized and shaped to receive removable platform 40. The shelf 35 further defines a flange 37 configured to extend inwardly along the periphery of opening 36 and support removable platform 40 to prevent platform 40 from falling through opening 36 into cavity 15. In application, a person wanting to remove the removable platform 40 and the contents on top of platform 40 may open door 10, push upward on a bottom surface of removable platform 40 until it has cleared opening 36, and then extract the removeable platform 40 through the door 10. In some embodiments, the flange 37 may include a plurality of fasteners (not shown) that removably attach the removable platform 40 to the flange 37 when fastened. The plurality of fasteners would need to be unfastened so that the removable platform 40 can be displaced from the flange 37. In one or more embodiments, the removable platform 40 is configured to be removable through the opening formed by the removal of subsection 13*d* and/or through the opening formed from removing removable access panel 65 as seen in FIG. 1.

As best seen in FIGS. 5, 6, 7, and 8, in one or more embodiments the scope cabinet 100 further comprises an air-circulating unit 45 that is positioned on the removable platform 40. The air-circulating unit 45 includes an electric fan 46, and more preferably a plurality of electric fans 46. The air-circulating unit 45 further includes a filter 48 and a filter holder 47 (FIGS. 6, 7), preferably a plurality of filters 48 and a plurality of filter holders 47, optimally one filter 48 and one filter holder 47 per two electric fans 46. In some embodiments, the filter holder 47 is formed from a rectangular base 47*a* and a side wall 47*b* that preferably extends from two lateral sides 47*c* and one longitudinal side 47*d* of the rectangular base 47*a*. The filter holder 47 is further configured to receive filter 48. The rectangular base 47*a* defines one or more openings 47*e* to facilitate the exchange of gases between the electric fan 46 and the filter 48. In alternative embodiments, the filter 48 and filter holder 47 may be any shape, but it is desirable for both to be formed in corresponding sizes and shapes. As demonstrated in FIG. 5 with portions removed for clarity the platform 40 further defines an opening 41 that is dimensioned to be slightly smaller than a bottom surface of an electric fan 46 so that the electric fan 46 may be positioned above the opening 41 without falling through. In the preferred embodiment, the opening 41 is a tight cluster of through holes. The opening 41 facilitates the exchange of gases from a portion of the cavity 15 above the removable platform 40 to a portion of the cavity 15 below the removable platform 40, creating positive pressure in the portion of the cavity 15 below the removable platform 40 and negative pressure in the portion of the cavity above the removable platform 40. The electric fan 46, filter 48, and filter holder 47, are arranged so that the electric fan 46 is positioned directly over opening 41, the filter holder 47 is stacked on top of electric fan 46, and filter 48 is inserted into the filter holder 47. In the preferred embodiment, there are two tight clusters of through-holes 41 arranged adjacent to one another with one electric fan 46 positioned above each cluster of through-holes 41, wherein a rectangular base 47*a* of filter holder 47 is sized and shaped to cover the two electric fans 46 and the filter holder 47 is configured to receive filter 48. In application, the electric fan 46 pulls gases from the portion of the cavity 15 above the removable platform 40 and pulls the gases through the filter 48 and then pushes the gases into the portion of the cavity 15 below the removable platform 40, creating positive pressure. The gases in the portion of the cavity 15 below the removable shelf 40 may exit through a gas outlet 67 as seen in FIG. 1 defined between the horizontal truss 18 and the bottom panel 12 and/or may exit through an elongated slat 66 defined through bottom panel 12, preferably there are two elongated slats 66. Maintaining positive pressure in the portion of the cavity 15 below the removable shelf 40 and filtering the air from the portion of the cavity 15 above the removable shelf 40 before being pushed into the portion of the cavity 15 below the shelf 40 mitigates the risk of pathogens, fungal spores, chemicals, allergens, and/or other undesirable particulates in the ambient air from being deposited onto sterilized internal scopes (not shown) contained within the cavity 15. Positive pressure prevents backflow of unfiltered, ambient air into cavity 15. The gases in the portion of the cavity 15 above the removable shelf 40 may enter this portion through an elongated slat 64 (best seen in FIG. 8) defined by the top panel 14, or through holes defined through subsection 13*d* of the rear panel 13. In the preferred embodiment, the filter 48 may be configured to remove pathogens, allergens, fungal spores, chemicals, and/or other undesirable particulates from the ambient air prior to the air being pushed into the portion of the cavity 15 below the removable shelf 40.

In one or more embodiments, the scope cabinet 100 further comprises a power unit 50 as seen in FIG. 5. The power unit 50 includes a power source 51 and a power distribution box 53 for wiring, preferably two power distribution boxes 53. The power distribution box 53 is electrically connected with the power source 51 via power cable 52. The power distribution box 53 is configured to distribute electricity from the power source 51 to the electric fan 46, preferably electric fans 46. The electric fan 46 and power distribution box 53 may be connected by power cable 52. The power distribution box 53 may include a circuit breaker switch 53*a* that is configured to trip in instances of electrical overload. In one or more embodiments, the power unit 50 includes a light source 54 configured to illuminate the portion of the cavity 15 below the removable platform 40. In the preferred embodiment, the light source 54 is an elongated LED bar that is configured to extend along a longitudinal axis of the removable platform 40 and may be positioned proximate to a side of the removable platform 40 nearest the door 10. The preferred elongated LED bar 54 is configured to be electrically connected to the power distribution box 53 via a power cable 52. In the preferred embodiment, the removable platform 40 defines an elongated slat 55 with a longitudinal length that is substantially the same as the longitudinal length as the elongated LED bar 54. The elongated LED bar 54 may be positioned over the elongated slat 55 so that light from the LED travels through the elongated slat 55 into the portion of the cavity below the removable platform 40, illuminating the cavity 15 and contents within the cavity 15. In certain embodiments, the removable platform may define two elongated slats 55, one positioned more proximate the door 10 and one positioned more proximate the rear panel 13. An elongated LED bar 54 is preferably placed directly on top of each of the two elongated slats 55. In the preferred embodiment, the scope cabinet 100 may include a door sensor 56 that is configured to activate the elongated LED bar 54 when the door 10 is in an open position (as seen in FIG. 1) and deactivate the elongated LED bar 54 when the door 10 is in a closed position (as seen in FIG. 2), in the ideal embodiment the door sensor 56 is a magnetic door sensor. The door sensor 56 may be electrically connected to the power distribution box 53 via power cable 52. Although not shown as understood a power cable would be included for attachment of power unit 50 to an external power source such as in the location of point of care or storage of scope cabinet 100.

In one or more embodiments, the power cables 52 of the electric fan 46 and elongated LED bar 54 may include a fastener 52*a* disposed at an end of the cable 52, wherein the power distribution box 53 may include corresponding fasteners 53*b* to the fasteners 52*a* of the power cable 52. In the preferred embodiment, the fasteners 52*a*, 53*b* are magnetic. The fasteners 52*a*,53*b* in combination with the plurality of fasteners 42 of the removable platform 40 and corresponding fasteners 46*a* of the electric fan 46 (best seen in FIG. 5) and the fasteners (not shown) of the elongated LED bar 54 facilitate the quick replacement and easy installation of electric fans 46 and elongated LED bars 54.

In certain embodiments, the removable platform 40 may include a plurality of fasteners 42 for attaching components of the air-circulating unit 45 and the power unit 50. The electric fan 46 includes a bottom fastener 46*a* and a top fastener 46*b*, positioned respectively on a bottom surface and a top surface of the electric fan 46. The bottom fastener 46*a* is attachable to one of the plurality of fasteners 42. The filter holder 47 includes a fastener 47*f* configured to be attachable to top fastener 46*b* so that the filter holder 47 remains on top of the electric fan 46 during operation of the electric fan 46 and during translocation of the scope cabinet 100. The power source 51 and power distribution box 53 each include fasteners (not shown) configured to be attached to one of the plurality of fasteners 42 to prevent unintended displacement from the removable platform 40 during transfer of the scope cabinet 100.

Now referring to FIG. 8, in the preferred embodiment, the top panel 14 defines a top access opening 60 sized and shaped so the air-circulating unit 45 and/or the power unit 50 on the removable platform 40 may be accessed by medical personnel without removing the removable platform 40 from the cavity 15. The top panel 14 further defines a flange 61 that extends along the periphery of the top access opening 60 and extends inward toward a center of the top panel 14. The scope cabinet 100 further comprises a top access panel 62 sized and shaped to be received by the top access opening 60 and supported by the flange 61. In some embodiments, a top portion of the flange 61 and a bottom portion of the top access panel 62 include corresponding fasteners 63, preferably magnets.

The medical devices used in connection with the scope cabinet 100 may be gastroscope, endoscopes, and similar devices. However, it should be understood by those skilled in the art that the medical devices used in connection with the scope cabinet may be any medical device.

The illustrations and examples provided herein are for explanatory purposes and are not intended to limit the scope of the appended claims.

We claim:

1. A cabinet comprising: a top panel, two side panels, a rear panel, a bottom panel, and a door, the top panel, the two side panels, the rear panel, the bottom panel, and the door assembled to define a cavity, the cavity configured to receive a medical device therein; a detachable cradle panel defining an elongated slat, the detachable cradle panel is releasably fastened to the rear panel and is disposed within the cavity; an adjustable arm comprising a base, and a plurality of fingers for receiving the medical device; an arm fastener, wherein, the arm fastener is insertable through the base and the elongated slat; wherein, the arm fastener, when fastened, is configured to prevent movement of the base along a longitudinal axis defined by the elongated slat.

2. The cabinet of claim 1, wherein the cabinet includes an air-circulating unit disposed within the cavity for maintaining airflow within the cavity, the air-circulating unit comprising an electric fan for circulating air.

3. The cabinet of claim 2, wherein the air-circulating unit includes a plurality of electric fans.

4. The cabinet of claim 3, wherein the air-circulating unit includes a plurality of filters, each filter of the plurality of filters positioned above and arranged in series with a respective electric fan of the plurality of electric fans.

5. The cabinet of claim 3, wherein the air-circulating unit includes a filter, the filter positioned above at least one of the electric fans and arranged in series with the electric fan so that air is pulled through the filter before being pushed by the fan into the cavity.

6. The cabinet of claim 5, wherein the cabinet includes a power unit, the power unit comprised of a power distribution box and a power source.

7. The cabinet of claim 6, wherein the power unit includes an elongated LED bar.

8. The cabinet of claim 7, wherein the cabinet includes a removable platform that is disposed within the cavity, adjacent to the top panel, the power unit and the air-circulating unit positioned on the removable platform, the removable platform defining an opening; the electric fan positioned directly above the opening, the opening sized and shaped so that the electric fan positioned over the opening will not fall through the opening, the opening is further configured to facilitate airflow from the electric fan in the direction of the bottom panel through the filter, thereby creating positive pressure in a portion of the cavity below the removable platform.

9. The cabinet of claim 7, wherein the cabinet includes a removable platform disposed within the cavity, adjacent to the top panel, the power unit and the air-circulating unit are positioned on the removable platform, the removable platform defining a plurality of through-holes; the electric fan positioned directly above the plurality of through-holes, the plurality of through-holes sized and shaped so that the electric fan positioned over the plurality of through-holes will not fall through the plurality of through-holes, the plurality of through-holes further configured to facilitate airflow from the electric fan in the direction of the bottom panel through the filter, thereby creating positive pressure in a portion of the cavity below the removable platform.

10. The cabinet of claim 7, wherein the top panel defines an access opening so that the air-circulating unit and power unit can be accessed through the access opening, the cabinet further comprising a removable top access panel sized and shaped to fully cover the access opening.

11. The cabinet of claim 1, wherein the detachable cradle panel defines a plurality of elongated slats.

12. The cabinet of claim 11, wherein the detachable cradle panel defines a plurality of openings that are arranged in an alternating pattern with the plurality of elongated slats.

13. The cabinet of claim 12, wherein the plurality of elongated slats are configured to extend along a longitudinal axis defined by the rear panel.

14. The cabinet of claim 1, wherein the rear panel defines three subsections arranged in series along a longitudinal axis of the rear panel, a first subsection positioned nearest the top panel and below the removable platform, wherein the detachable cradle panel is attached to the first subsection.

15. The cabinet of claim 1, wherein the rear panel defines three subsections arranged in series along a longitudinal axis of the rear panel, a first subsection positioned nearest the top panel and below the removable platform, a second subsection positioned nearest the bottom panel, a third subsection positioned between the first subsection and the second subsection, wherein at least one of the subsections is configured to receive the cradle panel.

* * * * *